United States Patent
Robinson

(10) Patent No.: US 10,024,836 B2
(45) Date of Patent: Jul. 17, 2018

(54) TRACE GAS MEASUREMENT APPARATUS FOR ELECTRICAL EQUIPMENT

(71) Applicant: General Electric Company, Schenectady, NY (US)

(72) Inventor: David Peter Robinson, Lisburn (GB)

(73) Assignee: General Electric Company, Schenectady, NY (US)

(*) Notice: Subject to any disclaimer, the term of this patent is extended or adjusted under 35 U.S.C. 154(b) by 78 days.

(21) Appl. No.: 14/669,871

(22) Filed: Mar. 26, 2015

(65) Prior Publication Data
US 2016/0282323 A1    Sep. 29, 2016

(51) Int. Cl.
| | | |
|---|---|---|
| *G01N 33/28* | (2006.01) | |
| *G01N 29/24* | (2006.01) | |
| *G01N 29/02* | (2006.01) | |
| *G01N 1/22* | (2006.01) | |

(52) U.S. Cl.
CPC ....... *G01N 33/2841* (2013.01); *G01N 1/2226* (2013.01); *G01N 29/02* (2013.01); *G01N 29/2418* (2013.01); *G01N 2001/2229* (2013.01); *G01N 2001/2241* (2013.01); *G01N 2291/021* (2013.01)

(58) Field of Classification Search
CPC ............... G01N 33/2841; G01N 29/02; G01N 29/2418; G01N 2291/021; G01N 21/3504; G01N 21/39
USPC ...................................................... 73/24.02
See application file for complete search history.

(56) References Cited

U.S. PATENT DOCUMENTS

| | | | |
|---|---|---|---|
| 3,779,066 A | | 12/1973 | Fore et al. |
| 4,385,634 A | * | 5/1983 | Bowen ................... A61B 5/416 600/407 |
| 4,890,478 A | | 1/1990 | Claiborne et al. |
| 4,944,178 A | | 7/1990 | Inoue et al. |
| 5,339,672 A | * | 8/1994 | Spicar ................ G01N 33/2841 210/188 |
| 5,400,641 A | | 3/1995 | Slemon et al. |
| 5,633,711 A | * | 5/1997 | Nelson ............... G01B 11/0666 356/318 |

(Continued)

FOREIGN PATENT DOCUMENTS

| | | | | |
|---|---|---|---|---|
| DE | 19503802 C1 | * | 3/1996 | ............. G01N 27/40 |
| DE | 19833601 C1 | * | 12/1999 | ............... G01N 7/10 |

(Continued)

OTHER PUBLICATIONS

Machine translation of DE 19503802 C1.*

(Continued)

*Primary Examiner* — Natalie Huls
*Assistant Examiner* — Monica S Young
(74) *Attorney, Agent, or Firm* — Parks IP Law LLC

(57) ABSTRACT

Provided, a trace gas measurement apparatus for electrical equipment that includes at least one sample cell configured to collect an oil sample from the electrical equipment. The sample cell includes (i) an oil receiving portion for receiving an oil sample, and (ii) a head space in an upper section thereof receiving ambient air therein, an oil pump for selectively pumping oil into and out of the sample cell, and a hydrogen gas sensor within an exhaust path of the sample cell. The hydrogen gas sensor receives the air exhausted from the sample cell and measures hydrogen gas present in the exhausted air.

16 Claims, 7 Drawing Sheets

(56) References Cited

U.S. PATENT DOCUMENTS

| | | | |
|---|---|---|---|
| 5,749,942 A | 5/1998 | Mattis et al. | |
| 6,037,592 A * | 3/2000 | Sunshine | G01N 21/3504 250/343 |
| 6,289,716 B1 * | 9/2001 | Lindgren | G01N 33/2841 73/19.1 |
| 6,391,096 B1 * | 5/2002 | Waters | B01D 19/0031 73/19.02 |
| 6,742,384 B2 | 6/2004 | Avila et al. | |
| 7,040,138 B2 * | 5/2006 | Braesel | G01N 33/2841 73/19.01 |
| 8,028,561 B2 | 10/2011 | Herz et al. | |
| 8,196,448 B2 * | 6/2012 | Kuebel | G01N 1/2252 422/98 |
| 8,395,777 B2 | 3/2013 | Roa et al. | |
| 2001/0044154 A1 * | 11/2001 | Evans | G01N 33/0013 436/144 |
| 2003/0172716 A1 * | 9/2003 | Braesel | G01N 33/2841 73/19.1 |
| 2009/0308246 A1 * | 12/2009 | Mahoney | B01D 19/0031 95/46 |
| 2010/0077828 A1 * | 4/2010 | Herz | G01N 33/2841 73/1.03 |
| 2011/0246088 A1 * | 10/2011 | Santos | G01N 33/2841 702/24 |
| 2012/0291521 A1 * | 11/2012 | Cavallini | G01N 33/2841 73/19.1 |
| 2013/0247647 A1 * | 9/2013 | Mahoney | G01N 33/0016 73/19.11 |
| 2014/0053626 A1 * | 2/2014 | Jeffrey | G01N 1/2035 73/19.1 |
| 2014/0165704 A1 * | 6/2014 | Maity | G01N 25/005 73/25.01 |
| 2014/0176936 A1 * | 6/2014 | Van Mechelen | G01N 21/3504 356/73 |
| 2014/0273261 A1 | 9/2014 | Panella et al. | |
| 2016/0054286 A1 | 2/2016 | Van Mechelen et al. | |
| 2016/0231303 A1 * | 8/2016 | Park | G01N 33/2841 |

FOREIGN PATENT DOCUMENTS

| | | | |
|---|---|---|---|
| EP | 1790965 A | 5/2007 | |
| EP | 2746747 A1 * | 6/2014 | G01N 21/3504 |
| JP | 60253842 A | 12/1985 | |
| WO | 2010042178 | 4/2010 | |
| WO | 2012135012 | 10/2012 | |
| WO | WO 2013116799 A1 * | 8/2013 | G01N 33/2841 |

OTHER PUBLICATIONS

Machine translation of DE 19833601 C1.*
European Search Report and Opinion issued in connection with corresponding EP Application No. 16161512.5 dated Jul. 21, 2016.
European Search Report and Written Opinion issued in EP Application No. 16161980.4 dated Jul. 21, 2016.

* cited by examiner

TRACE GAS MEASUREMENT APPARATUS FOR ELECTRICAL EQUIPMENT

I. TECHNICAL FIELD

The present invention relates generally to a trace gas measurement apparatus. In particular, the present invention relates to a trace gas measurement apparatus and methods of extracting trace gases (e.g., hydrogen gas) from ambient air injected into the trace gas measurement apparatus.

II. BACKGROUND

Trace gas in electrical equipment is commonly found in electrical insulating oil used in electrical equipment, which may perform any number of functions in generation, transmission and distribution of electrical power. Some examples of electrical equipment include transformers, tap-changers and circuit breakers. When a fault occurs within the electrical equipment, a trace gas (i.e., a fault gas) may be generated and becomes dissolved in the electrical insulating oil.

The trace gases are extracted from an oil sample obtained from the electrical equipment and measured by a measurement device. The trace gas measurements are used to provide an operational and health status of the electrical equipment. For example, in a transformer, when faults, e.g., arcing and overheating occur, gases such as methane and carbon dioxide or carbon monoxide are present in the insulating oil of the transformer. Measurements of these trace gases can be used to determine the type and the severity of the faults which occur in the electrical equipment.

A measurement device such as a photoacoustic spectroscope are typically used to obtain trace gas measurements such as methane, ethane, ethylene and other trace gases with the exception of hydrogen, where small vibrations of the molecules in the trace gases are generated when subjected to a particular infrared (IR) frequencies of light. Hydrogen is generated as a result of several fault conditions, e.g., oil or other insulation overheating, oxidation issues and arcing. In addition, the presence of hydrogen in trace gases is indicative of a low energy potential difference.

III. SUMMARY OF THE EMBODIMENTS

The various embodiments of the present disclosure are configured to provide a trace gas measurement apparatus having a hydrogen gas sensor for extracting and measuring hydrogen gas exhausted from a sample cell of the trace gas measurement apparatus.

In one exemplary embodiment, a trace gas measurement apparatus is provided. The trace gas measurement apparatus for electrical equipment includes at least one sample cell configured to collect an oil sample from the electrical equipment. The sample cell includes (i) an oil receiving portion for receiving an oil sample, and (ii) a head space in an upper section thereof receiving ambient air therein, an oil pump for selectively pumping oil into and out of the sample cell, and a hydrogen gas sensor within an exhaust path of the sample cell. The hydrogen gas sensor receives the air exhausted from the sample cell and measures hydrogen gas that is present in the exhausted air.

In another exemplary embodiment, a method of extracting hydrogen gas in a trace gas measurement apparatus having a sample cell is provided. The method includes performing a flushing operation of the sample cell using ambient air; pumping oil into the sample cell and filling the sample cell to a top surface thereof; pushing air into an exhaust path of the sample cell; and measuring, via a hydrogen gas sensor within the exhaust path, hydrogen gas present in the air exhausted.

The foregoing has broadly outlined some of the aspects and features of various embodiments, which should be construed to be merely illustrative of various potential applications of the disclosure. Other beneficial results can be obtained by applying the disclosed information in a different manner or by combining various aspects of the disclosed embodiments. Accordingly, other aspects and a more comprehensive understanding may be obtained by referring to the detailed description of the exemplary embodiments taken in conjunction with the accompanying drawings, in addition to the scope defined by the claims.

IV. DESCRIPTION OF THE DRAWINGS

Figure 1:
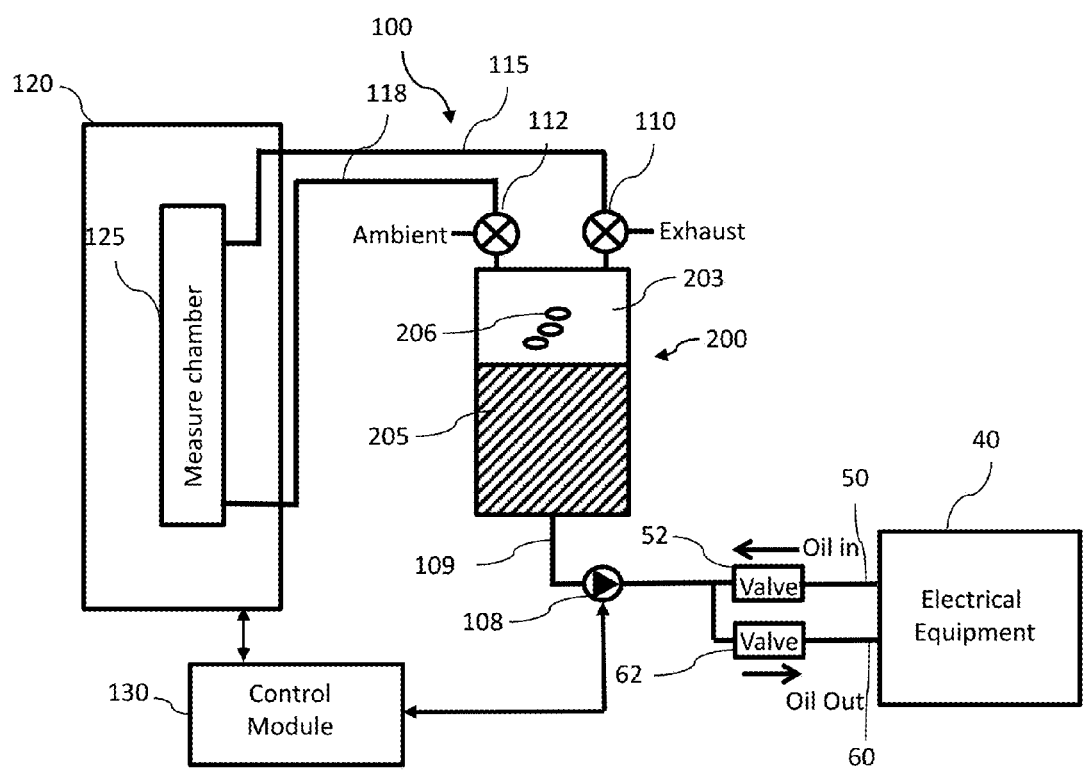
FIG. 1 is a block diagram illustrating a trace gas measurement apparatus that can be implemented within one or more embodiments of the present invention.

The drawings are only for purposes of illustrating preferred embodiments and are not to be construed as limiting the disclosure. Given the following enabling description of the drawings, the novel aspects of the present disclosure should become evident to a person of ordinary skill in the art. This detailed description uses numerical and letter designations to refer to features in the drawings. Like or similar designations in the drawings and description have been used to refer to like or similar parts of embodiments of the invention.

V. DETAILED DESCRIPTION OF THE EMBODIMENTS

As required, detailed embodiments are disclosed herein. It must be understood that the disclosed embodiments are merely exemplary of various and alternative forms. As used herein, the word "exemplary" is used expansively to refer to embodiments that serve as illustrations, specimens, models, or patterns. The figures are not necessarily to scale and some features may be exaggerated or minimized to show details of particular components. In other instances, well-known components, systems, materials, or methods that are known to those having ordinary skill in the art have not been described in detail in order to avoid obscuring the present disclosure. Therefore, specific structural and functional details disclosed herein are not to be interpreted as limiting, but merely as a basis for the claims and as a representative basis for teaching one skilled in the art.

Exemplary embodiments of the present invention provides a trace gas measurement apparatus for performing dissolved gas analysis (DGA) on electrical insulating oil flowing within electrical equipment (e.g., transformers, circuit breakers, or tap changers). The trace gas measurement apparatus may be implemented within a portable gas analyzer (PGA).

The DGA process is used to determine the health (e.g., the occurrence and nature of any faults or failure) of the electrical equipment and the current state of operation thereof. The trace gas measurement apparatus effectively performs hydrogen gas extraction and detection using hydrogen gas sensor, by adjusting the air pressure level within a sample cell in communication with the hydrogen gas sensor. Therefore, the extraction method of the present invention provides the advantages of increasing the amount of hydrogen gas to be extracted and effectively detects the hydrogen gas extracted.

FIG. 1 is a block diagram illustrating a trace gas measurement apparatus that can be implemented within one or more embodiments of the present invention. As shown in FIG. 1, the trace gas measurement apparatus 100 is connectable to and communicates directly with electrical equipment 40. This communication may be performed in real-time, on-line during operation of the electrical equipment 40. The trace gas measurement apparatus 100 may be disposed in direct contact with the electrical equipment 40 or in a remote location while maintaining communication with the electrical equipment 40.

The present invention is not limited to the trace gas measurement apparatus 100 being disposed in any particular location, the location may be any location suitable for the purposes set forth herein. Further, the present invention is not limited to the electrical equipment including any particular type or number of electrical equipment components (e.g., transformers, tap changers, and/or circuit breakers), and may vary accordingly.

The trace gas measurement apparatus 100 includes at least one sample cell 200 corresponding to and connectable to the electrical equipment 40, and including a head space 203 and an oil sample 205 housed therein. The sample cell 200 collects the oil sample 205 of insulating oil flowing through the electrical equipment 40, from which trace gases 206 such as methane, ethane, ethylene, acetylene, carbon monoxide and carbon dioxide are to be extracted for analysis. A laser-based sensor or other sensor system may be employed for receiving the trace gases 206 from the sample cell 200 and performing the trace gas detection process, to determine the health of the electrical equipment 40.

The trace gas measurement apparatus 100 further includes an oil pump 108 connected with the sample cell 200 for selectively pumping oil into or out of the sample cell when necessary, via forward and return oil flow lines 50 and 60 connecting to the electrical equipment 40. The forward and return oil flow lines 50 and 60 respectively including valves 52 and 62, for controlling the flow of oil to the oil pump 108 from the electrical equipment 40, and from the oil pump 108 to the electrical equipment 40.

According to embodiments, the oil pump 108 is a reversible type oil pump for selectively reversing the operation thereof, to either pump oil into or out of the sample cell 200. The oil pump 108 is not limited to any particular type of reversible pump. Further, alternatively, separate pumps may be used to separately pump oil into and out of the sample cell 200. Any pump(s) suitable for the purpose set forth herein may be employed.

Further, the valves 52 and 62 are non-reversible valves (NRVs) which prevent oil being supplied from the electrical equipment 40 or to the electrical equipment 40 from reversing in direction and causing damage to the extraction process. The present invention is not limited to any particular type or number of valves, any type or number of valves suitable for the purpose set forth herein may be employed.

Further, a plurality of valves 110 and 112 within respective forward and return gas paths 115 and 118 are provided. The forward and return gas paths 115 and 118 connect the sample cell 200 to an analysis module 120, for performing measurements and analysis on trace gases 206 extracted within the sample cell 200.

The analysis module 120 includes a measure chamber 125 for receiving trace gases 206 therein, and performing DGA. A control mechanism (not shown) may be provided for controlling the stop and start of flow and amount of flow within the forward and return paths 115 and 118.

A control module 130 is also provided in communication with the analysis module 120, and oil pump 108 and controls operations within the trace gas measurement apparatus 100.

Further as shown, the oil sample 205 in the sample cell 200 is supplied via the forward flow line 50 from the electrical equipment 40 to the sample cell 200 during operation of the trace gas measurement apparatus 100. The oil sample 205 resides in the sample cell 200 for a predetermined period of time during which a measurement and analysis operation is to be performed. Although a single sample cell 200 is provided, a plurality of sample cells 200 may be provided to accommodate multiple electrical equipment components as needed. Alternatively, multiple electrical equipment components may be connected to a single sample cell 200.

FIGS. 2A through 2D are detailed schematics of a sample cell 200 which may be employed within the trace gas measurement apparatus 100 of FIG. 1, illustrating operations thereof that can be implemented within one or more embodiments of the present invention.

Figure 2A:
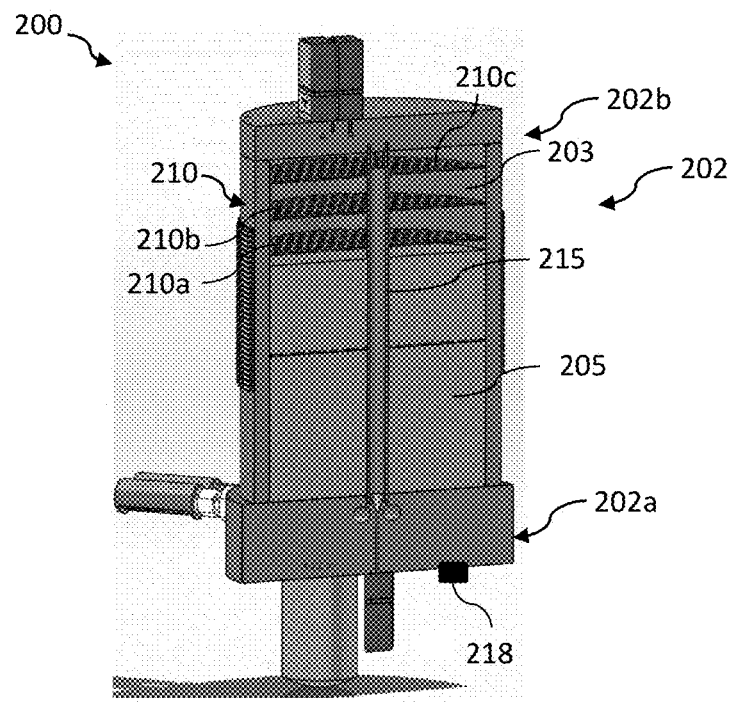
FIGS. 2A through 2D are detailed schematics of a sample cell of the trace gas measurement apparatus of FIG. 1, illustrating operations thereof that can be implemented within one or more embodiments of the present invention.

As shown in FIG. 2A, the sample cell 200 comprises a housing 202 having a lower section 202a and an upper section 202b, for housing an oil sample 205 therein. The oil sample 205 enters the sample cell 200 through an opening in the lower section 202a. The sample cell 200 further includes a plurality of perforated sheets 210 including 210a, 210b and 210c disposed in a fixed horizontal manner by a fixing means (not shown) within the upper section 202b of the housing 202 in the head space region 203. The perforated sheets 210 are spaced a predetermined distance apart.

An oil receiving portion 215 extends in a vertical direction through the housing 202, and receives new oil samples from the electrical equipment 40 via line 109 as depicted in FIG. 1. According to an embodiment, the oil receiving portion 215 may be in the form of a tube or piping for receiving and transmitting oil to the sample cell 200. A separate oil output portion 218 is also included in the sample cell 200 for outputting existing oil samples from the sample cell 200. The inputting of new oil samples and outputting of existing oil samples is controlled by the control module 130 (as depicted in FIG. 1).

Figure 2B:
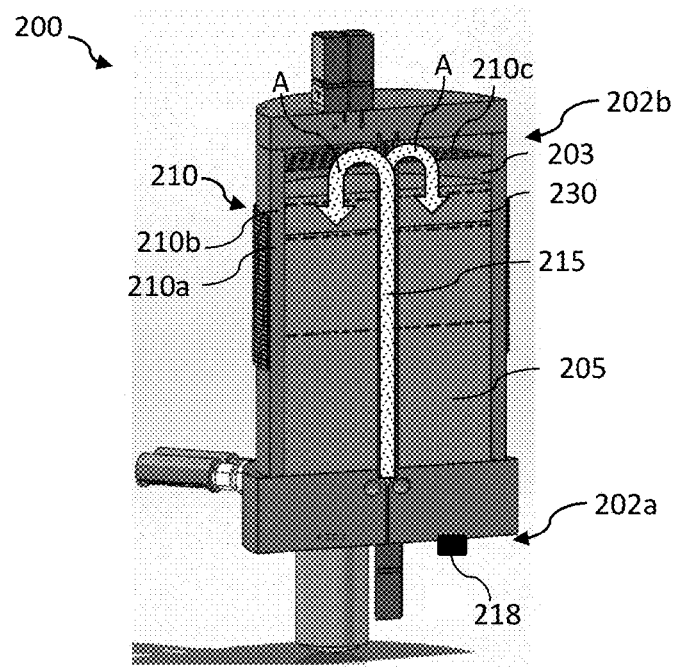
Figure 2C:
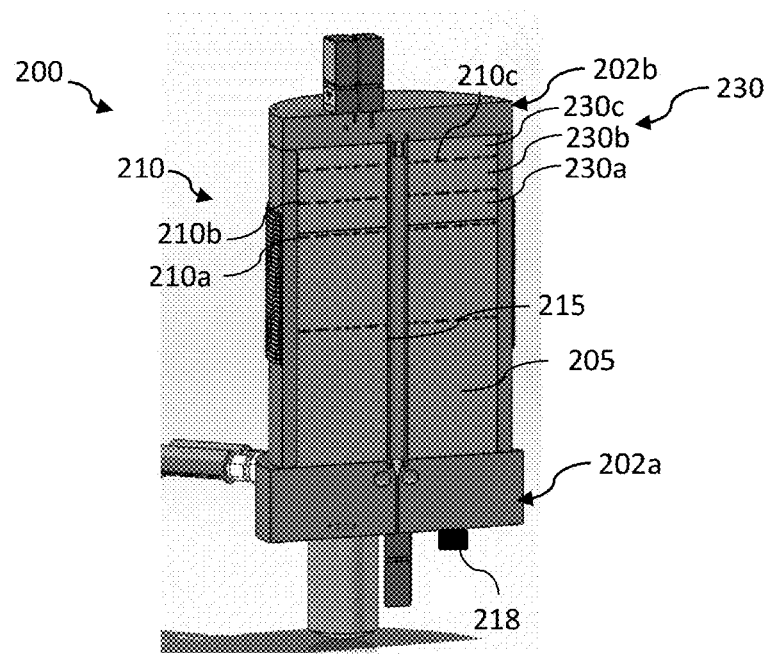
Figure 2D:
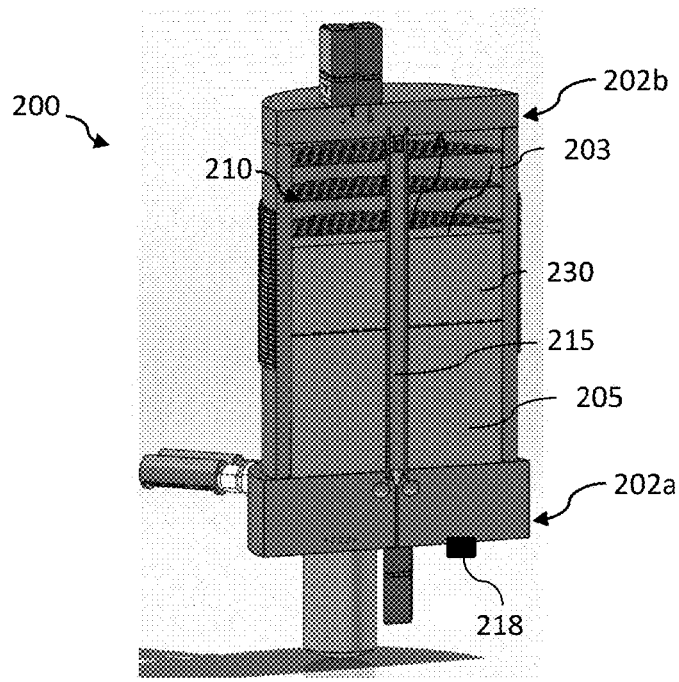

As shown in FIGS. 2B through 2D, in operation of the sample cell 200, valve 52 (as depicted in FIG. 1) is open to allow an oil sample 205 from the electrical equipment 40 to be drawn and pumped via the oil pump 108 into the sample cell 200. When a new oil sample 230 is desired during the measurement process, oil portions 230a, 230b and 230c of the oil sample 230 are pumped successively via the oil pump 108 through the oil receiving portion 215 and into the upper section 205b (see arrows 'A') and are disposed on the first, second and third perforated sheets 210a, 210b and 210c.

Further as shown in FIG. 2B, when the oil portion 230a is pumped into the sample cell 200 the weight of the oil portion 230a pushes the first perforated sheet 210a towards a top surface of the existing oil sample 205 and rest thereon, forming a liquid film on the sheet 210a. As shown in FIG. 2C, the surface area (i.e., the head space 203 as depicted in FIG. 2B) for the extraction process is minimized since the oil level is at its maximum level.

The perforated sheets 210 prevent the new oil sample 230 from comingling and recirculation with the existing oil sample 205. The present invention is not limited to any particular number or type of perforated sheets and may vary accordingly. For example, the perforated sheets may be bent perforated sheets (e.g., an upturned U shape) arranged in a circular form or a stack of perforated sheets as shown in FIG. 2A.

Next in FIG. 2D, when the trace gases 206 as depicted in FIG. 1 are to be extracted, the existing oil sample 205 is pumped out from oil output portion 218 in the lower section 202a of the housing 202, leaving the new oil sample 230 in the sample cell 200. Then, the oil remaining in the sample cell 200 is equalised, to thereby obtain trace gases 206 (as depicted in FIG. 1).

The process is repeated multiple cycles by adding new oil sample 230 and pumping out existing oil sample 205 and extracting trace gases 206 (as depicted in FIG. 1) from the oil sample remaining in the sample cell 200. The oil pump 108 as depicted in FIG. 1, provides a volume pressure which further assist in extracting gas from the oil samples 205, 230. The present invention provides the advantage of being able to extract an increased amount of trace gases including hydrogen gas.

Additional details regarding the extraction process will be discussed below with reference to FIGS. 3A through 3F.

Figure 3A:
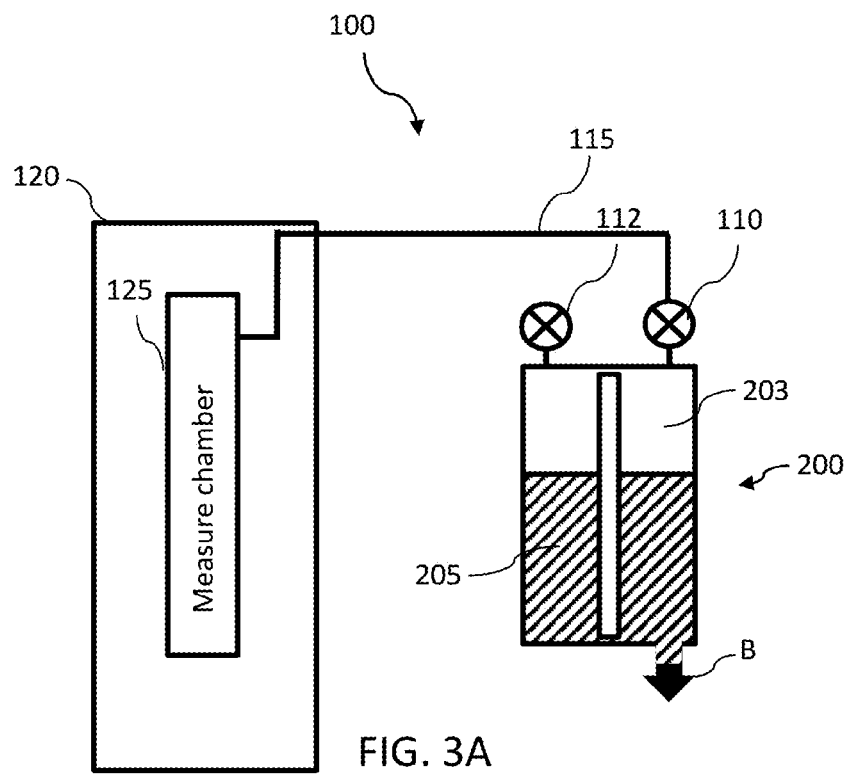
FIGS. 3A through 3F are block diagrams of the trace gas measurement apparatus of FIG. 1, illustrating trace gas extraction operations performed on air exhausted from the sample cell that can be implemented within one or more embodiments of the present invention.

FIGS. 3A through 3F are block diagrams of the trace gas measurement apparatus of FIG. 1, illustrating trace gas extraction operations using air exhausted from the sample cell that can be implemented within one or more embodiments of the present invention. As shown in FIG. 3A, at the initiation of the extraction process, a flushing operation is performed by inputting a new ambient gas sample (i.e., atmospheric air sample) which contains a minimal amount of trace gases, e.g., zero (0) parts per million (ppm) of acetylene, into the apparatus 100 via the ambient valve 112. The oil level is dropped in the sample cell 200 by pumping the oil out (as depicted by arrow 'B') and the ambient valve 112 is opened to receive the air sample, and air within the measure chamber 125 is also drawn into the sample cell 200 via the exhaust valve 110.

Figure 3B:
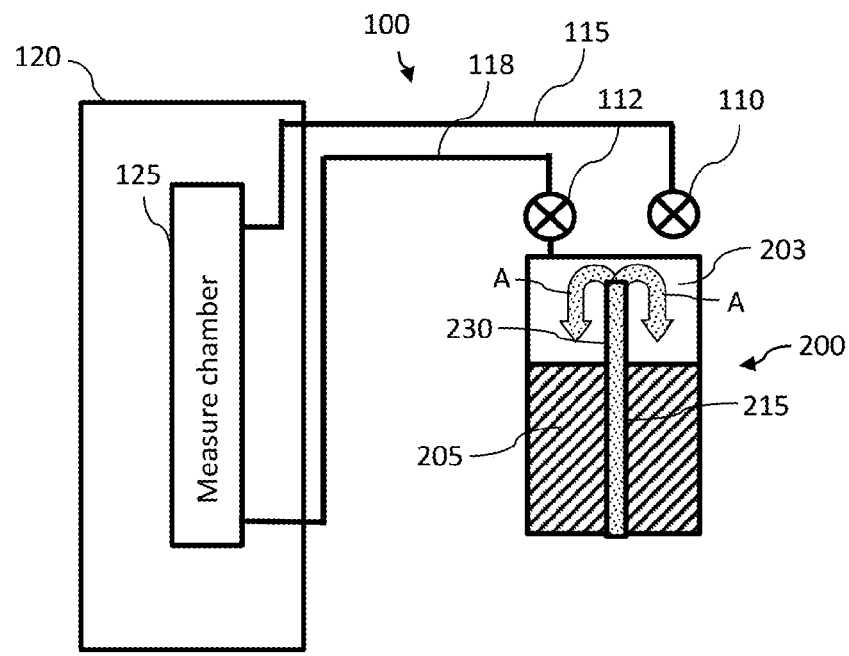

After measuring the trace gases (not shown) within the air sample, to exhaust the air sample, exhaust valve 110 is opened, air is pushed out through the exhaust valve 110 by filling the oil level with new oil 230 as shown in FIG. 3B (see arrows 'A').

Figure 3C:
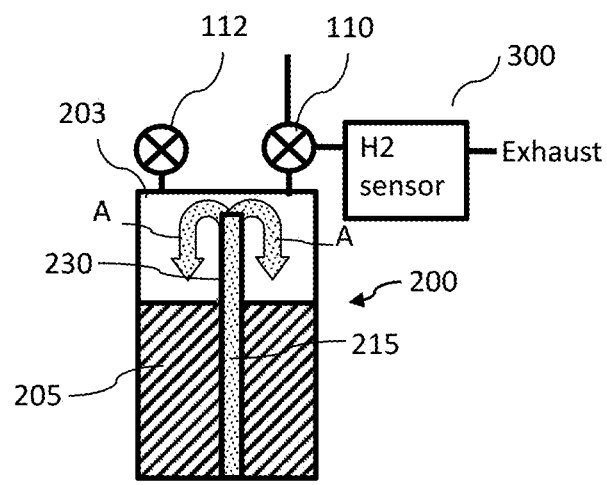

As shown in FIG. 3C, to initiate the extraction process, the sample cell 200 is filled to a top surface with oil from oil sample 205 and the valves 110 and 112 The valves 110 and 112 are then closed. As shown in FIG. 3C, the trace gas measurement apparatus 100 further includes a hydrogen (H2) sensor 300 within the exhaust path. The hydrogen gas sensor 300 is in ambient air within an enclosed volume having a small opening to allow the hydrogen gas sensor to be recharged by atmospheric levels of gases (i.e., oxygen).

Figure 3D:
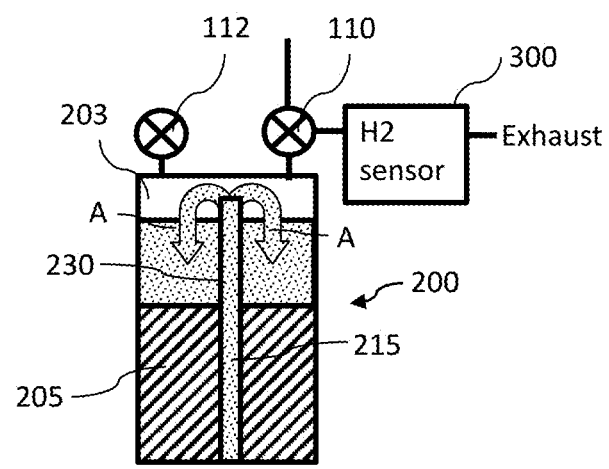

As the oil 230 fills the sample cell 200, as shown in FIG. 3D, the pressure within the sample cell 200, pushes air flow within the head space 203 through the exhaust valve 110 and into the hydrogen gas sensor 300. The pressure may be approximately 1.1 bar. However, the pressure within the sample cell 200 is not limited hereto and may vary as necessary. For example, since the hydrogen gas sensor 300 is sensitive to flow velocities, applying a small amount of pressure increase of approximately 0.1 bar over ambient will enable control thereof.

Figure 3E:
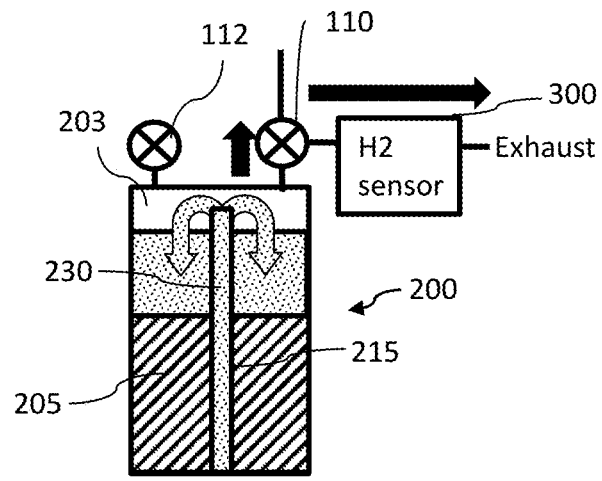

As shown in FIG. 3E, the exhaust valve 110 is opened for a predetermined time to exhaust air (see arrows), for example, approximately 0.25 seconds to approximately 30 seconds for a plurality of increments, to determine the concentration of hydrogen gas in the air exhausted. By performing this process in increments of short bursts, there is an increase in the H2 measurement over time. The present invention is not limited to a particular predetermined time or number of increments to be performed, and may vary accordingly.

Figure 3F:
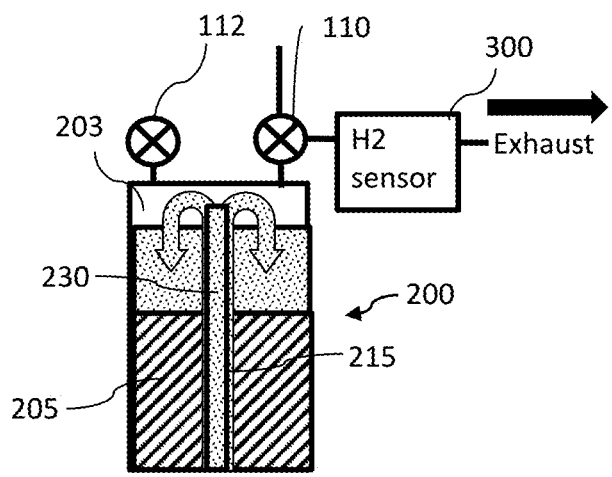

Next in FIG. 3F, the exhaust valve 110 is closed and the trace gas measurement apparatus 100 monitors the rise and decay within the hydrogen gas sensor 300 and reads the peak measurement at the dilution of the volume within the hydrogen gas sensor 300 during the plurality of increments.

Referring back to FIG. 1 and FIGS. 2A through 2D, the extraction of other trace gases is performed by adding new oil sample 230 into the sample cell 200 via the oil receiving portion 215 (see arrows 'A') and the sample cell 200 is filled to the top surface, and removing existing oil from the sample cell 200 using the oil output portion 218, continuously repeating multiple cycles, to allow trace gases to be extracted from the oil in the sample cell 200 as desired, at a lower detection limit (LDL) such as approximately 1 ppm (parts per million).

Alternatively, the oil level within the sample cell 200 may be adjusted along with other measuring parameter such as the air pressure within the sample cell 200, in order to extract the trace gases from the oil at a higher detection limit (HDL) for example, approximately 50,000 ppm. Both of these extraction processes are described in co-pending Application entitled TRACE GAS MEASUREMENT APPARATUS FOR ELECTRICAL EQUIPMENT by David Robertson et al., the application in its entirety is incorporated herein by reference.

As mentioned, the extraction processes are performed under the control of the control system 130 as shown in FIG. 1. The control module 130 includes a microcontroller or microprocessor programmed with computer software for controlling the extraction process and performing analysis of the trace gases 206 when supplied to the analysis module 120. The control module 130 controls the operation of the analysis module 120 and the oil pump 108. The control module 130 may be any type of computing device capable of performing the operations of the present invention.

Figure 4:
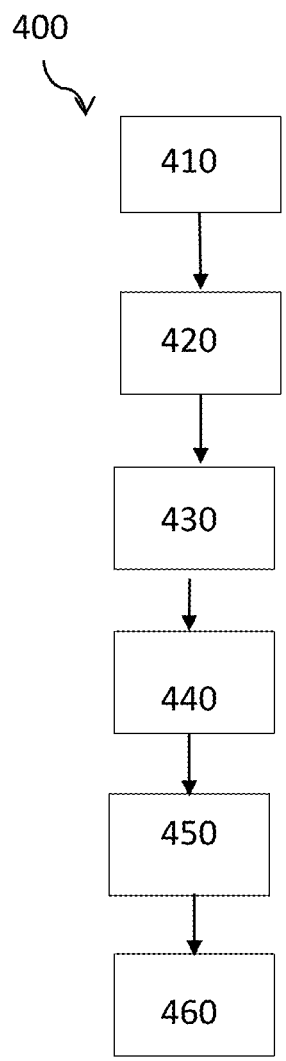
FIG. 4 is a flow diagram illustrating an exemplary hydrogen gas extraction method illustrated in FIGS. 3A through 3F, implementing an embodiment of the present invention.

FIG. 4 is a flow diagram illustrating an exemplary hydrogen gas extraction method 400 as illustrated in FIGS. 3A through 3F, implementing an embodiment of the present invention. The process begins at operation 410, where an ambient gas sample containing trace gases is input into the sample cell of the trace gas measurement apparatus (FIG. 3A).

From operation 410, the process continues to operation 420, where the oil level is dropped in the sample cell (FIG. 3A) and air within the analysis module is drawn into the sample cell to perform (FIG. 3B), and a measurement of the trace gases within the air sample is performed.

The process then continues to operation 430, where new oil is input into the sample cell (FIG. 3C) and the oil level is increased to pressurize the sample cell and force the air within the sample cell to be exhausted through an exhaust valve and into a hydrogen gas sensor (FIG. 3D).

At operation 440, the exhaust valve is opened for a predetermine time period to determine a concentration of hydrogen gas therein (FIG. 3E). At operation 450, the exhaust valve is closed and the rise and decay in the hydrogen gas sensor is measured and the peak measurement is taken during an application of dilution of the sensor volume for example, two times, three times, etc. (FIG. 3F).

According to one or more embodiments of the present invention, the exhaust valve is opened and closed in several increments each for a predetermined period of time such as 0.25 seconds in order to determine the concentration of hydrogen gas within the hydrogen gas sensor. The present invention is not limited to any particular number of increments or any particular predetermined time period and may vary accordingly.

In operation 460, the sample cell is then filled with new oil, existing oil is withdrawn from an oil output portion to a predetermined level, and the air pressure is adjusted to measure trace gases within the oil in the sample cell. The exhaust valve is opened to allow the filled oil chamber to be at approximately 1 bar absolute, before repeating the process.

The trace gas measurement apparatus of the present invention may be used in an on line measurement type arrangement with electrical equipment such as a main transformer and/or tank changer. The measurement apparatus may further be implemented in real-time to determine the condition of the total electrical system (e.g., a transformer system). These faults can be detected early, to minimize cost associated with unplanned outages and any electrical equipment failure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A trace gas measurement apparatus for electrical equipment, the trace gas measurement apparatus comprising: an analysis module including a measure chamber for receiving trace gases therein, wherein the analysis module is configured to perform dissolved gas analysis; a sample cell configured to collect an oil sample from the electrical equipment, wherein the sample cell comprises: an oil receiving portion configured to direct oil into an upper section of the sample cell, wherein a level of oil in the sample cell defines a head space above the level of oil; and an oil output portion configured to direct oil out of a lower section of the sample cell; a forward gas path connecting the analysis module to the head space of the sample cell; an oil pump for selectively pumping oil into the sample cell through the oil receiving portion; an exhaust outlet path connecting to the head space of the sample cell and including an exhaust outlet, wherein the exhaust outlet path includes a hydrogen gas sensor, wherein the hydrogen gas sensor is configured to measure hydrogen gas flowing through the exhaust outlet path; wherein the exhaust outlet path extends from the forward gas path at a point that is upstream from the analysis module; an exhaust valve configured to control flow from the head space through the exhaust outlet path; and a control module configured to: close air flow paths into and out of the head space and operate the pump to pump oil into the sample cell through the oil receiving portion, thereby increasing the level of oil in the sample cell and the pressure in the head space, thereby providing a pressurized head space; and operate the exhaust valve to control flow from the pressurized head space through the exhaust outlet path, wherein the exhaust valve is opened for a plurality of consecutive increments, each of the plurality of consecutive increments comprising a predetermined amount of time, to allow flow from the pressurized head space through the exhaust outlet path, wherein the exhaust valve is closed after each of the plurality or consecutive increments thereby maintaining pressure in the head space sufficient to generate flow from the pressurized head space through the exhaust outlet path; and operate, for each increment of the plurality of consecutive increments, the hydrogen gas sensor to perform a measurement of hydrogen gas flowing through the exhaust outlet path.

2. The trace gas measurement apparatus of claim 1, wherein the oil receiving portion is configured to direct oil into the upper section of the sample cell on a top surface of existing oil within the sample cell.

3. The trace gas measurement apparatus of claim 1, wherein the hydrogen gas sensor is in ambient air in an enclosed volume having a small opening to allow the hydrogen gas sensor to be recharged by atmospheric levels of gases.

4. The trace gas measurement apparatus of claim 1, wherein the predetermined amount of time is 0.25 seconds to 30 seconds.

5. The trace gas measurement apparatus of claim 1, wherein the hydrogen gas sensor is configured to measure a rise and decay and peak readings of the dilution of volume.

6. The trace gas measurement apparatus of claim 1, wherein the control module is further configured to control the analysis module.

7. The trace gas measurement apparatus of claim 1, wherein the exhaust valve is at an intersection of the exhaust outlet path and the forward gas path, wherein the intersection is upstream from the analysis module.

8. The trace gas measurement apparatus of claim 1, wherein the hydrogen gas sensor is between an intersection of the exhaust outlet path and the forward gas path and the exhaust outlet, wherein the intersection is upstream from the analysis module.

9. The trace gas measurement apparatus of claim 1, wherein the hydrogen gas sensor is separated from the forward gas path.

10. The trace gas measurement apparatus of claim 1, wherein the exhaust outlet path is separated from the forward gas path.

11. The trace gas measurement apparatus of claim 1, wherein the exhaust outlet path and the forward gas path are separated such that flow from the head space does not flow through both the analysis module and the hydrogen gas sensor.

12. The trace gas measurement apparatus of claim 1, wherein a perforated sheet is positioned in the sample cell between an upper point where the oil receiving portion directs oil into the upper section of the sample cell and a lower point where the oil output portion directs oil out of the sample cell.

13. The trace gas measurement apparatus of claim 12, wherein the perforated sheet is fixed in a horizontal manner within the sample cell.

14. The trace gas measurement apparatus of claim 12, wherein the perforated sheet is configured to deter comingling of oil that is received in the sample cell above the perforated sheet through the oil receiving portion with oil that is within the sample cell below the perforated sheet.

15. The trace gas measurement apparatus of claim 12, comprising a plurality of perforated sheets.

16. The trace gas measurement apparatus of claim 15, wherein the plurality of perforated sheets are horizontal and spaced apart.

* * * * *